US011246707B2

(12) United States Patent
Zerkowski et al.

(10) Patent No.: US 11,246,707 B2
(45) Date of Patent: Feb. 15, 2022

(54) ANNULOPLASTY IMPLANT

(71) Applicant: Medtentia International Ltd Oy, Espoo (FI)

(72) Inventors: Hans-Reinhard Zerkowski, Kreuzlingen (CH); Olli Keränen, Bjärred (SE)

(73) Assignee: Medtentia International Ltd Oy, Espoo (FI)

( * ) Notice: Subject to any disclaimer, the term of this patent is extended or adjusted under 35 U.S.C. 154(b) by 0 days.

(21) Appl. No.: 16/758,710

(22) PCT Filed: Oct. 26, 2018

(86) PCT No.: PCT/EP2018/079516
§ 371 (c)(1),
(2) Date: Apr. 23, 2020

(87) PCT Pub. No.: WO2019/081775
PCT Pub. Date: May 2, 2019

(65) Prior Publication Data
US 2021/0177597 A1 Jun. 17, 2021

Related U.S. Application Data

(60) Provisional application No. 62/578,066, filed on Oct. 27, 2017.

(30) Foreign Application Priority Data

Oct. 27, 2017 (EP) .................................... 17199059

(51) Int. Cl.
*A61F 2/24* (2006.01)

(52) U.S. Cl.
CPC .......... *A61F 2/2445* (2013.01); *A61F 2/2466* (2013.01); *A61F 2210/0014* (2013.01);
(Continued)

(58) Field of Classification Search
CPC .... A61F 2/2442; A61F 2/2445; A61F 2/2448; A61F 2/2454; A61F 2/2457; A61F 2/246;
(Continued)

(56) References Cited

U.S. PATENT DOCUMENTS

| 2004/0167620 A1* | 8/2004 | Ortiz ..................... A61F 2/2445 |
| | | 623/2.11 |
| 2007/0250161 A1 | 10/2007 | Dolan | |
| 2008/0071364 A1* | 3/2008 | Kaye ..................... A61F 2/2445 |
| | | 623/2.11 |

FOREIGN PATENT DOCUMENTS

| EP | 2591755 A1 | 5/2013 |
| WO | 2006091163 A1 | 8/2006 |
| WO | 2015023579 A1 | 2/2015 |

OTHER PUBLICATIONS

International Search Report for International Application No. PCT/EP2018/079516, dated Jan. 18, 2019 (4 pages).

* cited by examiner

*Primary Examiner* — Brian A Dukert
*Assistant Examiner* — Rebecca Lynee Zimmerman
(74) *Attorney, Agent, or Firm* — Kagan Binder, PLLC

(57) ABSTRACT

An annuloplasty implant is disclosed comprising first and second supports being adapted to be arranged as a coil in a coiled configuration around an axial direction. The first and second supports are adapted to be arranged on opposite sides of native heart valve leaflets. The first support comprises first retention units fixed in relation to an outer surface of the first support and arranged along at least a first retention portion thereof. The second support comprises second retention units fixed in relation to an outer surface of the second support and arranged along at least a second retention portion thereof. First and second retention portions are curved in the coiled configuration, and the first and second
(Continued)

retention units extend from respective first and second retention portions to produce a retention force, in use, at both of said opposite sides. A method of repairing a defective heart valve is also disclosed.

25 Claims, 13 Drawing Sheets

(52) U.S. Cl.
CPC ............... *A61F 2220/0016* (2013.01); *A61F 2230/0091* (2013.01)

(58) Field of Classification Search
CPC ............ A61F 2/2466; A61F 2230/0091; A61F 2250/006
See application file for complete search history.

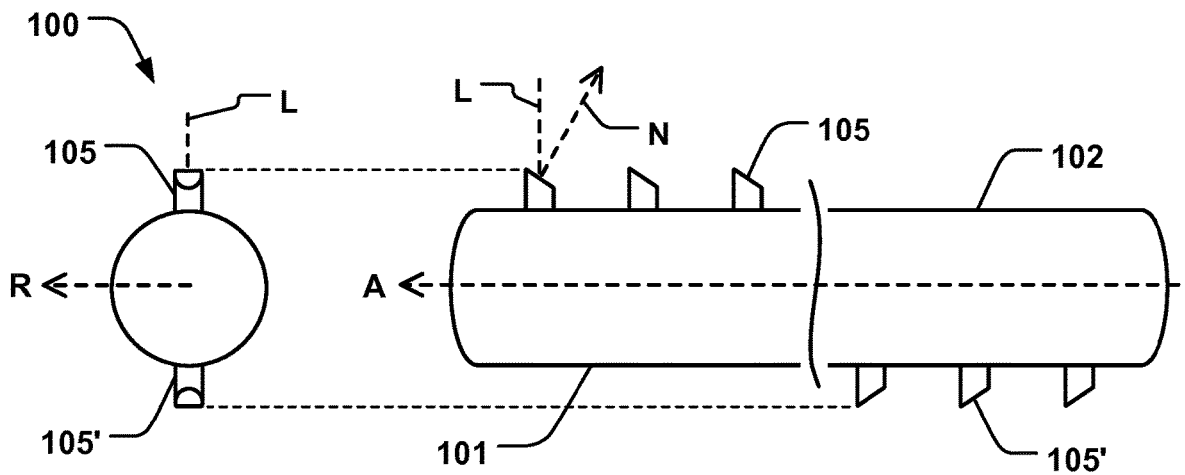
Fig. 8a    Fig. 8b
Fig. 8c
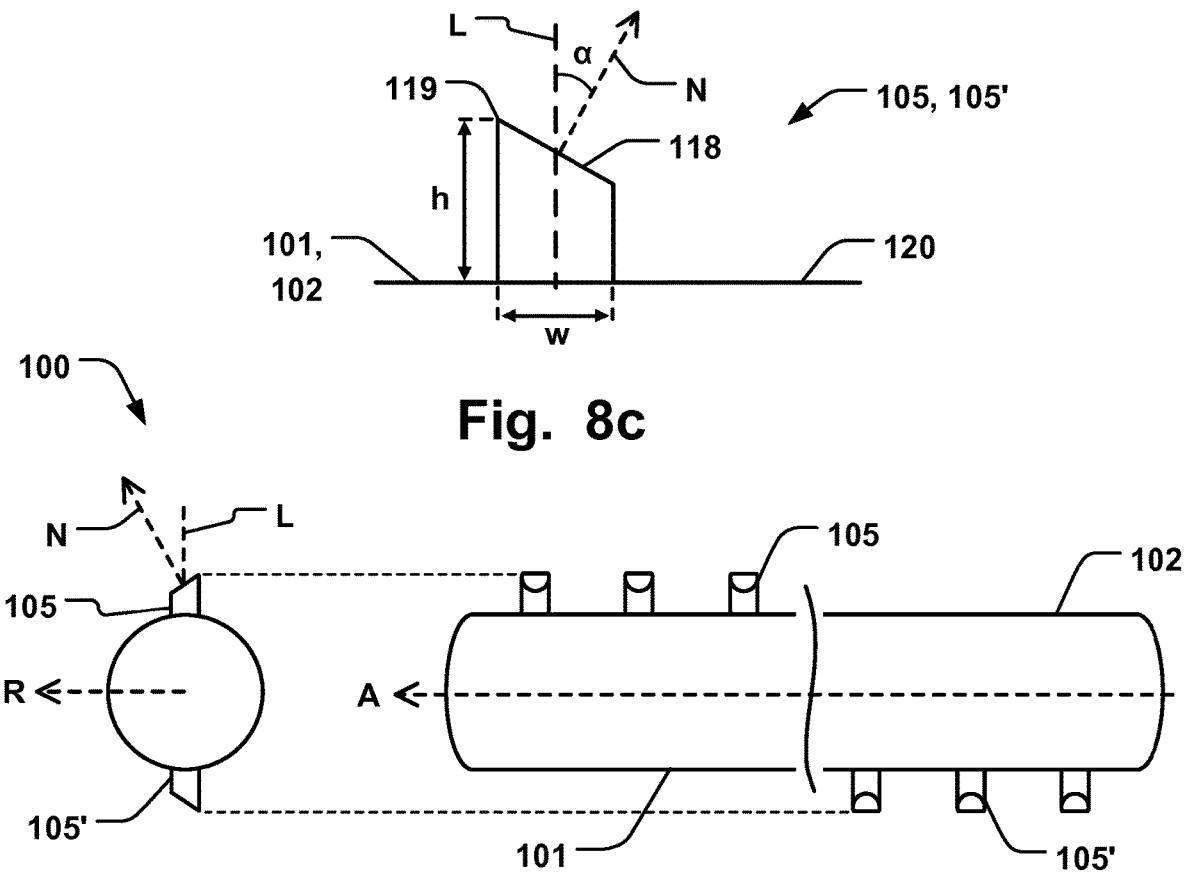
Fig. 9a    Fig. 9b

ANNULOPLASTY IMPLANT

CROSS-REFERENCE TO RELATED APPLICATIONS

This application claims priority to International Application No. PCT/EP2018/079516, filed Oct. 26, 2018 and titled "ANNULOPLASTY IMPLANT," which in turn claims priority from a European Application 17199059.1 filed Oct. 27, 2017, and a U.S. Provisional Patent Application No. 62/578, 066 filed Oct. 27, 2017, titled "ANNULOPLASTY IMPLANT," both of which are incorporated herein by reference in their entireties.

FIELD OF THE INVENTION

This invention pertains in general to the field of cardiac valve repair. More particularly the invention relates to an annuloplasty implant, such as an annuloplasty ring or helix, for positioning at the heart valve annulus and a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. The annuloplasty ring is typically implanted around the annulus of the heart valve.

A problem with prior art annuloplasty implants is to achieve correct positioning at the heart valve and fixate the implant in the correct position. Suturing devices for annuloplasty implants have disadvantages that makes it difficult to suture in the correct position, thereby resulting insufficient suturing strength, and also in a very time-consuming procedure, which increases the risks for the patient. Furthermore, suturing devices are often not sufficiently compact for catheter based procedures. The use of clips for positioning annuloplasty implants is also associated with challenges, in particular when implanting helix rings that are to be positioned on either side of a heart valve. Insufficient fixation of such implant lead to traumatic effects since the fixation structure must ensure the correct position of the device over time. A further problem in the prior art is thus also to achieve a reliable fixation at the annulus of the heart valve. An annuloplasty implant is intended to function for years and years, so it is critical with long term stability in this regard.

The above problems may have dire consequences for the patient and the health care system. Patient risk is increased.

Hence, an improved annuloplasty implant would be advantageous and in particular allowing for avoiding more of the above mentioned problems and compromises, and in particular ensuring secure fixation of the annuloplasty implant, during the implantation phase, and for long-term functioning, in addition to a less complex procedure, and increased patient safety. A related method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty implant is provided comprising first and second supports being adapted to be arranged as a coil in a coiled configuration around an axial direction. The first and second supports are adapted to be arranged on opposite sides of native heart valve leaflets of a heart valve. The first support comprises first retention units fixed in relation to an outer surface of the first support and arranged along at least a first retention portion thereof. The second support comprises second retention units fixed in relation to an outer surface of the second support and arranged along at least a second retention portion thereof. The first and second retention portions are curved in the coiled configuration, and the first and second retention units extend from respective first and second retention portions to produce a retention force, in use, at both of said opposite sides.

According to a second aspect a method of repairing a defective heart valve is provided. The method comprises directing an implant delivery catheter to form a first curve of the implant delivery catheter around the heart valve at a first side of native heart valve leaflets thereof, forming a second curve of the delivery catheter around the heart valve on a second side of the heart valve leaflets opposite the first side, and ejecting an annuloplasty implant from the delivery catheter while retracting the delivery catheter such that the annuloplasty implant is arranged along the first and second curve on the first and second sides, whereby retention units arranged on the annuloplasty implant are engaged into tissue of the heart valve from both the first side and the second side when the delivery catheter is retracted.

Further examples of the invention are defined in the dependent claims, wherein features for the second aspect are as for the first aspect mutatis mutandis.

Some examples of the disclosure provide for a facilitated positioning of an annuloplasty implant at a heart valve.

Some examples of the disclosure provide for a facilitated fixation of an annuloplasty implant at a heart valve.

Some examples of the disclosure provide for a less time-consuming fixation of an annuloplasty to a target site.

Some examples of the disclosure provide for securing long-term functioning and position of an annuloplasty implant.

Some examples of the disclosure provide for a reduced risk of damaging the anatomy of the heart such as the annulus or the valve leaflets.

Some examples of the disclosure provide for facilitated guidance of an annuloplasty implant to an annulus of a heart valve.

Some examples of the disclosure provide for a more secure implantation of an annuloplasty implant in narrow anatomies.

Some examples of the disclosure provide for avoiding interference of the annuloplasty implant with the chordae of the valve leaflets.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 8a-b are schematic illustrations of an annuloplasty implant, in a cross-sectional view (8a), and in a side view (8b), respectively, according to examples of the disclosure;

FIG. 8c is a magnified view of a retention unit in FIGS. 8a-b;

FIGS. 9a-b are schematic illustrations of an annuloplasty implant, in a cross-sectional view (9a), and in a side view (9b), respectively, according to examples of the disclosure;

DESCRIPTION OF EMBODIMENTS

Figure 1:
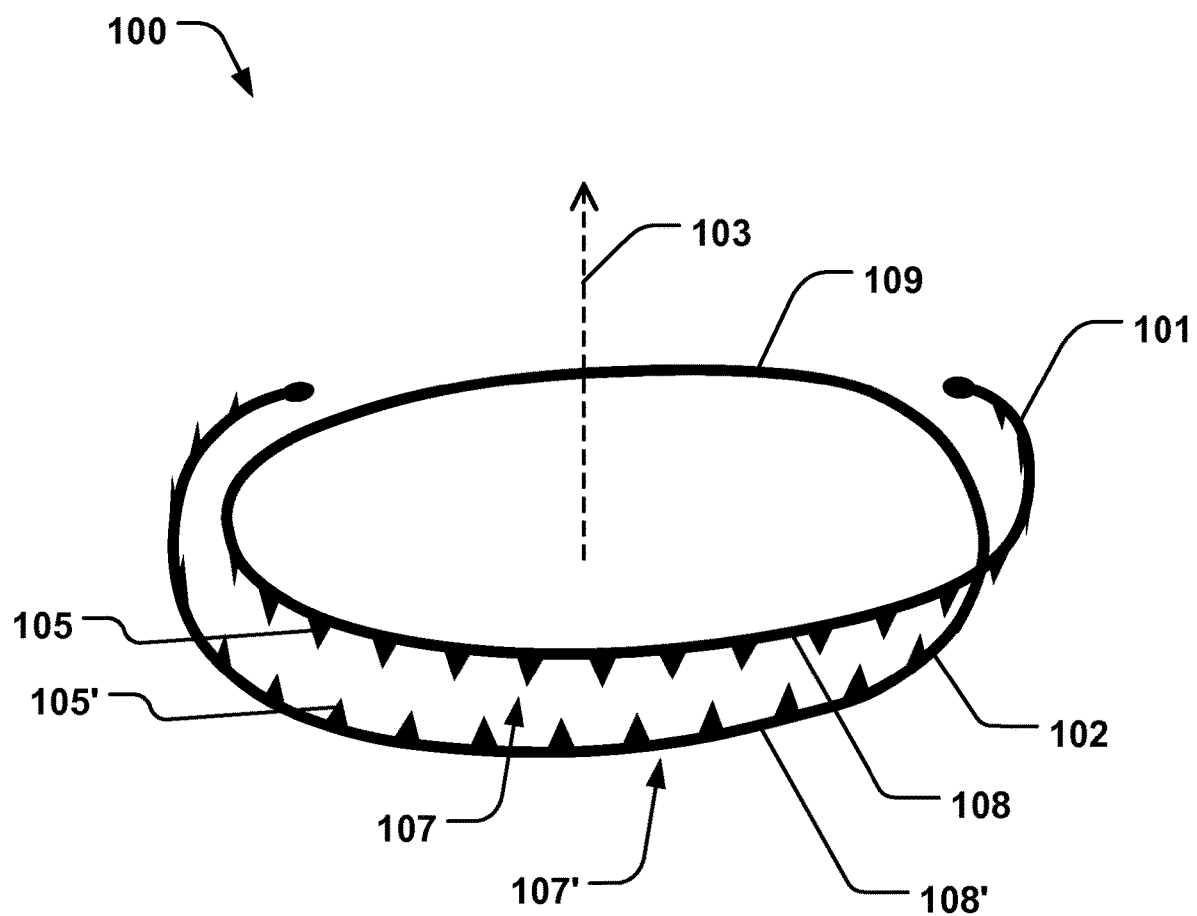
FIG. 1 is a schematic illustration of an annuloplasty implant according to an example.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 2:
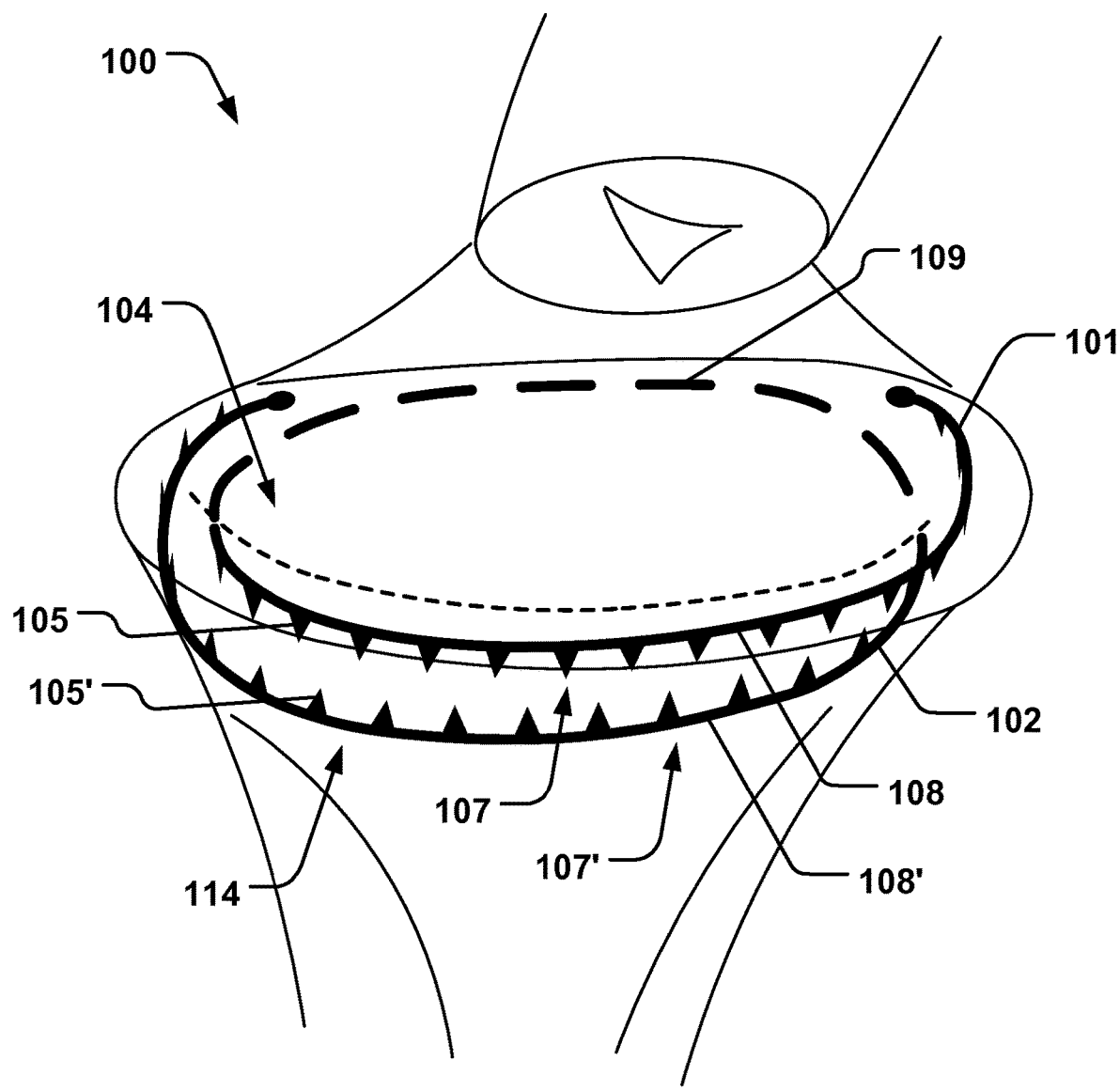
FIG. 2 is a schematic illustration of an annuloplasty implant, when in an implanted state, according to an example.
Figure 3A:
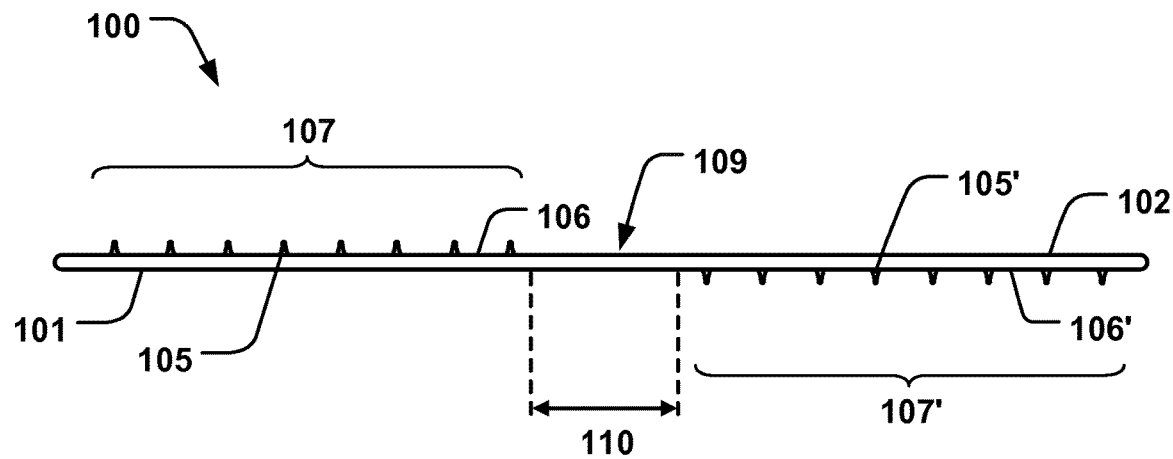
FIGS. 3a-b are schematic illustrations of an annuloplasty implant, when in a stretched elongated configuration, according to examples of the disclosure.
Figure 3B:
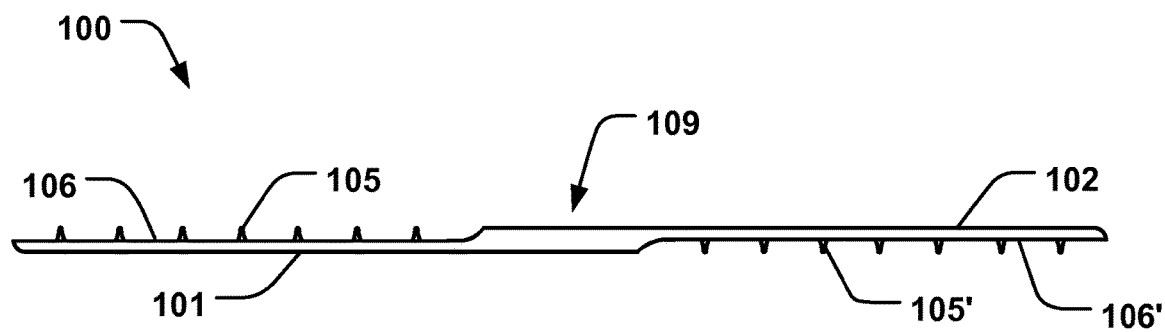

FIG. 1 is a schematic illustration of an annuloplasty implant 100 comprising first 101 and second 102 supports being adapted to be arranged as a coil in a coiled configuration around an axial direction 103. The first and second supports 101, 102, are adapted to be arranged on opposite sides of native heart valve leaflets 104 of a heart valve, as illustrated in FIG. 2. As shown in FIG. 2, the first support 101 may be arranged on an atrial side of the valve, and the second support 102 may be arranged on a ventricular side. The first and second supports 101, 102, are connected to form a coil- or helix shaped ring. The coil extends through the valve opening (dashed line) at a commissure thereof. In the examples of FIGS. 1-2, the second support 102 forms a complete loop, whereas the first support 101 has a reduced length along its periphery, as will be described further below. The implant 100 may comprise a shape-memory material, so that the implant 100 assumes the coiled configuration after having been ejected from a delivery catheter. While in the delivery catheter the implant 100 may be stretched in an elongated shape, i.e. as illustrated in FIGS. 3a-b. Alternatively, the implant 100 may be arranged in the coiled configuration when being delivered to the target site, in which case it may be implanted at the target site for example by incision between the ribs or by opening the chest. The present disclosure, and the associated advantages described for the various examples, applies to both such variants of the implant 100. The first support 101 comprises first retention units 105 fixed in relation to an outer surface 106 of the first support 101 and arranged along at least a first retention portion 107 thereof. The second support 102 comprises second retention units 105' fixed in relation to an outer surface 106' of the second support and arranged along at least a second retention portion 107' thereof. The retention units 105, 105', are illustrated in the perspective views of FIGS. 1 and 2, and in the schematic side views of FIGS. 3a-c of the implant 100 when stretched in an elongated shape, as well in cross-sectional views of FIGS. 3e-f. As seen in FIGS. 1 and 2, the first and second retention portions 107, 107', are curved in the coiled configuration. Hence, the retention units 105, 105', are arranged to extend along the curved shape of the coil- or helix shaped implant 100. The first retention portion 107 may be configured to follow the curvature of the annulus of the heart valve, such as the mitral- or tricuspid valve. The second retention portion 107' may be configured to follow the shape of the valve from the ventricular side. The first and second retention units 105, 105', extend from respective first and second retention portions 107, 107', to produce a retention force, in use, at both of said opposite sides of the native heart valve leaflets. Having retention units 105, 105', at both sides of the valve provides for increasing the retention force and the strength by which the annuloplasty implant 100 is fixated at the valve. The first retention units 105 pierce and anchor into the tissue at a first side of the valve independently of the second retention units 105' which pierce and anchor into the tissue at a second side, opposite the first side. This provides for having the first support 101 repositionable relative the second support 102 since any interlocking therebetween can be dispensed with. This provides for a facilitated optimization of the position of the first and second supports 101, 102, at opposite sides of the heart valve. The retention units 105, 105', engage the tissue from both of the mentioned sides, creating a strong retention force in the radial direction, i.e. perpendicular to the axial direction 103. The first and second supports 101, 102, pinch the tissue from both sides of the valve, so that the retention units 105, 105', a forced into the tissue. The retention units 105, 105', provides for shaping the annulus as desired even with a reduced pinching force, since the retention units 105, 105', provides for fixating the shape of the annulus in the radial direction because of the mentioned retention force. This provides for a more reliable implantation at the heart valve, both in the short term and in the long term. By having the first and second retention units 105, 105', fixed in relation to a respective outer surface 106, 106', a robust, less complex and more readily implementable fixation mechanism can be provided, since there is no need for e.g. active retention mechanisms that are activated to move relative the outer surface 106, 106. The aforementioned fixed position in relation to the respective outer surface 106, 106', may be construed as having the retention units 105, 105', attached to the first and second supports 101, 102, at a pre-defined position during manufacturing, or integrated with the first and second supports 101, 102, at a pre-defined position during manufacturing. As illustrated in e.g. FIG. 1, a plurality of retention units 105, 105', may be provided on the respective first and second supports 101, 102. Each individual retention unit 105, 105' may engage or pierce into the tissue with a short distance, for a minimum amount of injury to the tissue. The sum of the retention force and friction created from all the retention units 105, 105', still provides for a strong fixation into the tissue. The scar healing will be quick since each individual retention unit 105, 105', as relatively small dimensions. This provides for a non-traumatic and still secure fixation of the implant 100. Hence, the retention units 105, 105', provides for tissue fixation at multiple points across the implant 100 in stead of a few, e.g. 5 or 7 isolated stiches, resulting in reduced forces per fixation point, and no need for bulky stitching device or knotting device. There is further no risk of coronary artery occlusion or coronary sinus perforation. Hence, the implant 100 provides for ease of operation, and a less time consuming procedure than stitching.

The first retention units 105 may extend from the first retention portion 107 in a direction towards the second support 102. This allows the first retention units 105 to be securely fixed in to the tissue in the direction where the pinching force may be strongest.

Likewise, the second retention units 105' may extend from the second retention portion 107' in a direction towards the first support 101, so that the second retention units 105' may engage or pierce into the tissue effectively.

The first and second retention units 105, 105', may extend in opposite directions along the axial direction 103, as illustrated in the example in e.g. FIG. 1. I.e. the first and second retention units 105, 105', may extend from respective retention portions 107, 107', towards each other, to clamp the tissue therebetween. It is conceivable however that the retention units 105, 105', may extend in different directions. The first retention units 105 may for example extend with an angle in a radially outward direction to engage tissue in a direction towards a tissue wall radially outside the annulus.

Figure 5A:
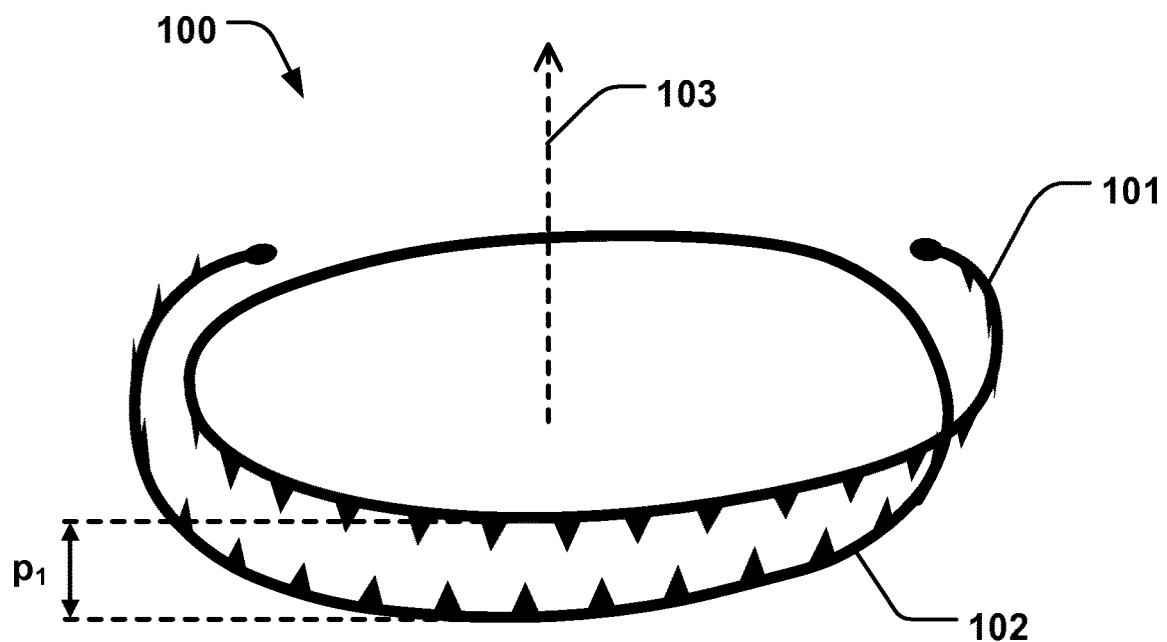
FIGS. 5a-b are schematic illustration of an annuloplasty implant, having supports thereof separated by defined pitch distances, according to examples of the disclosure.
Figure 5B:
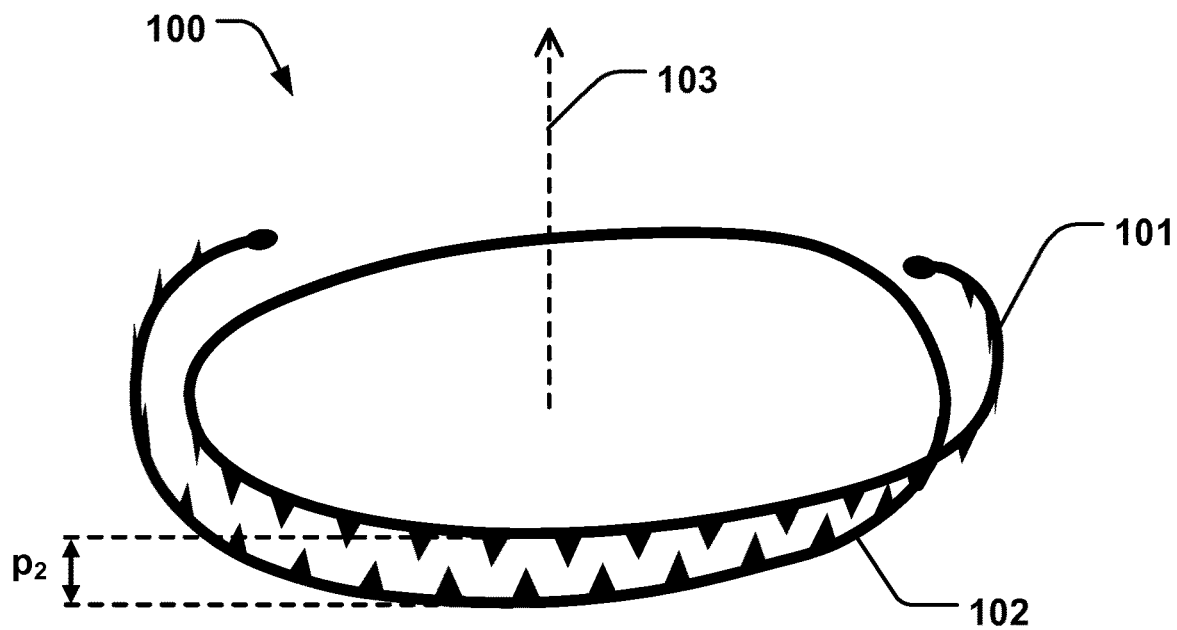

The first and second supports 101, 102, may be separated with a first pitch distance ($p_1$) in the axial direction 103, in the coiled configuration, as illustrated in FIG. 5a. The first and/or second support may comprise a shape-memory material configured to assume a contracted state having a second pitch distance ($p_2$) in the axial direction 103 being shorter than the first pitch distance ($p_1$), as illustrated in FIG. 5b. Thus, the first and second supports 101, 102, may contract along the axial direction due to movement of the shape-memory material. This provides for increasing the force by which the annuloplasty implant 100 is fixed at the annuls, and the retention units 105, 105', may engage the tissue with an increased force from both sides of the valve. The annuloplasty implant 100 may be arranged at the valve when assuming the first pitch distance ($p_1$). The shape-memory material may then be activated so that the contracted state is assumed, with the reduced distance ($p_2$) between the supports 101, 102, and the retention portions 107, 107', thereof.

The shape-memory material may be configured to assume the contracted state in response to an activation temperature. For example, the temperature may be increased to an activation temperature, so that the annuloplasty implant assumes the contracted state with a reduced pitch distance ($p_2$). It is conceivable that the implant 100 may be kept at a defined temperature while arranged in a delivery catheter. Subsequently, when the implant 100 is exposed to the warm tissue, when being ejected from the delivery catheter, the activation temperature may be reached, so that the first and second supports 101, 102 contracts towards each other and the retention units 105, 105', can be forced into the tissue. A delivery catheter 301 is illustrated in FIGS. 6a-c, 7a-c, which will be described further below.

The implant 100 may comprise a shape memory material, such as NiTiNol, or another suitable biocompatible alloy that can be heat-set in defined shapes, in a heat treatment procedure. The shape-memory material may comprise a material having more than one phase, so that the shape of the supports 101, 102, may be actively varied as described above. The shape memory material can be conceived as any material that is able to change shape as desired, in response to outside interaction, for example with an energy source, such as providing heat and/or electromagnetic energy, that can be transferred to the implant to change its shape. It is also conceivable that the shape of the implant can be affected by direct mechanical manipulation of the curvature of the ring-shape of the implant 100, e.g. by transferring a force or torque to the implant 100 via a delivery device. Via the various mentioned shape-affecting procedures the implant 100 may assume an elongated delivery configuration for advancement in a catheter, an initial shape when positioned in a coiled configuration along the annulus of the valve, and also an activated shape such as the contracted state described above for enhancing the strength of the fixation at an annulus of the heart valve.

The first and second supports 101, 102, may be configured to engage with a restraining unit at a separation at the first pitch distance ($p_1$) and to assume the contracted state upon removal of the restraining unit. This provides for facilitating the positioning of the implant 100 at both sides of the valve, since the pitch distance ($p_1$) may first be increased to avoid undesired friction with the tissue or entanglement with parts of the anatomy. The restraining unit may comprise a delivery catheter 301, which may be positioned around the annulus as described further below with reference to FIGS. 6a-c, 7a-c, while the first and second supports 101, 102, assumes the curvature of the delivery catheter 301 with a first pitch distance ($p_1$). When the delivery catheter 301 is retracted, exposing the annuloplasty implant 100, the first and second supports 101, 102, may contract to the reduced pitch distance ($p_2$). It is conceivable however that the implant 100 may engage with various other restraining units, such as biodegradable elements that allows the implant 100 to assume its contracted shape after being biodegraded or in other ways removed.

Figure 4:
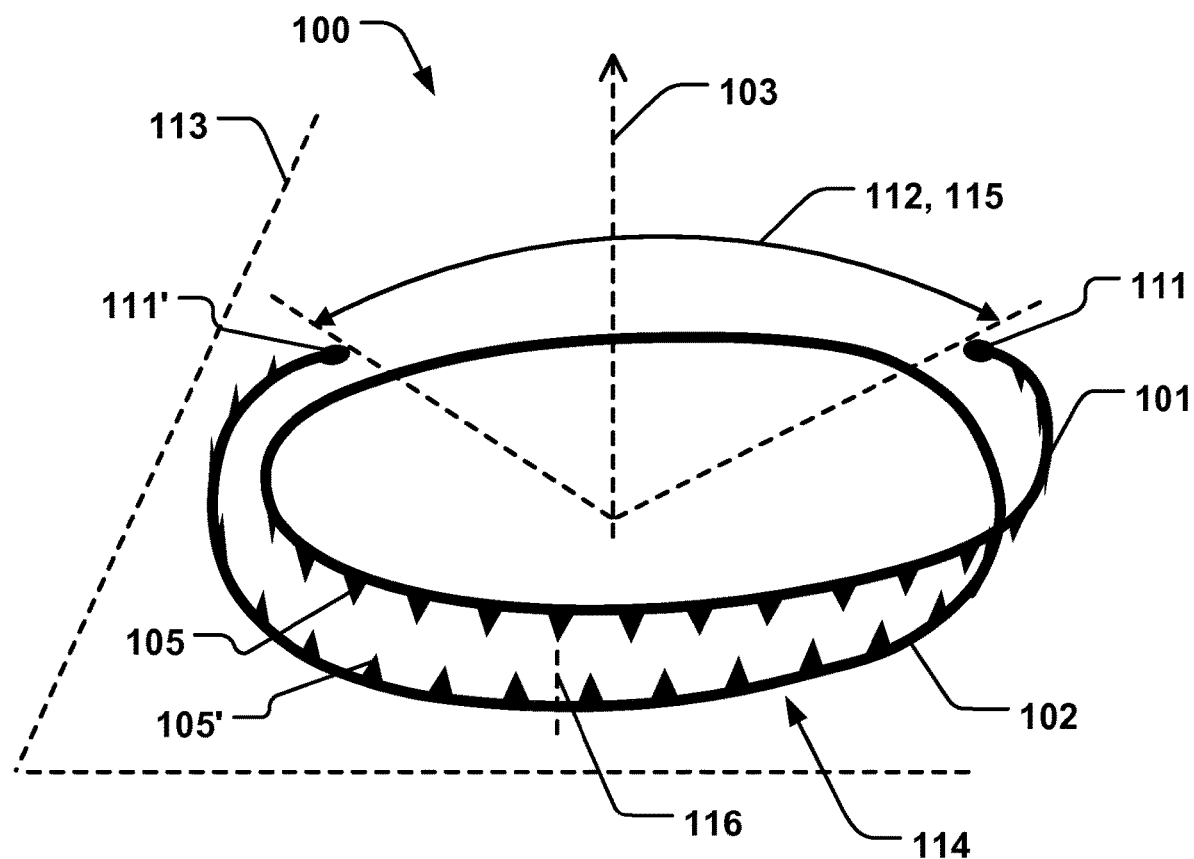
FIG. 4 is a schematic illustration of an annuloplasty implant according to an example.

At least part of the first retention units 105 may be displaced in a direction along an annular periphery 114 of the coil in relation to at least part of the second retention units 105'. A line 116 extending from a first retention unit 105, parallel with the axial direction 103, may thereby intersect the annular periphery 114 of the second support 102 at a position between two second retention units 105'. FIG. 4 illustrates the first and second retention units 105, 105', being displaced in relation to each other, so that the first retention units 105 may move towards a position between the second retention units 105' (as illustrated by dashed line 116). This may provide for further increasing the retention strength, while minimizing the risk that the retention units 105, 105', pierce completely through the valve tissue. This risk for complications is thereby reduced.

At least part of the first and second retention units 105, 105', may comprise a shape that tapers in a direction from the respective first and second retention portions 107, 107', as illustrated in the examples of e.g. FIGS. 1, 3c-f. This may provide for facilitating pushing and/or piercing of the retention units 105, 105', into the tissue, while scars are kept at a minimum. The retention units 105, 105', may comprise other structures configured to engage the tissue, such as barbs, needles etc.

The first support 101 may be adapted to be arranged on an atrial side of the heart valve, and the second support 102 may be adapted to be arranged on a ventricular side of the heart valve. The first support 101 may comprise a first posterior bow 108 and the second support 102 comprises a second posterior bow 108'. The first and second posterior bows 108, 108', may be adapted to conform to a posterior aspect of the heart valve. The first and second retention units 105, 105, may be arranged on respective first and second posterior bows 108, 108', as illustrated in FIGS. 1-2. This provides for avoiding piercing the tissue at an anterior side 109 of the annuloplasty implant, which can be associated with a greater risk of complications.

Figure 3C:
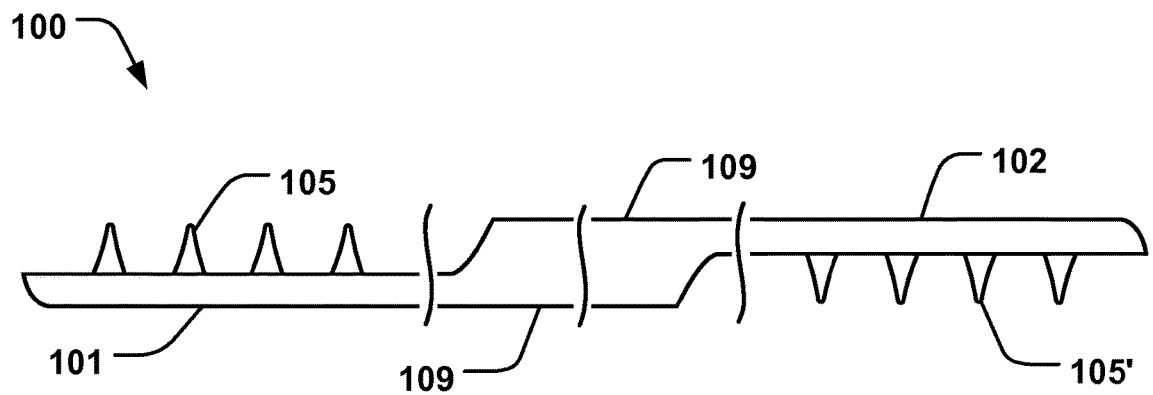
FIG. 3c is a magnified view of sections of the annuloplasty implant in FIG. 3b, according to an example.

Hence, the first and second posterior bows 108, 108', may be separated by an intermediate anterior portion 109. The first and second retention units 105, 105', may be arranged with an off-set distance 110 from the anterior portion 109 towards respective first and second posterior bows 108, 108', so that the anterior portion 109 may comprise a smooth surface free from retention units 105, 105'. FIGS. 3a-c also show illustrations of the anterior portion 109 positioned between the first and second retention portions 107, 107', when the implant 100 is in the elongated stretched state. The off-set distance 110 may be varied to optimize the annuloplasty implant to the particular anatomy while ensuring that there is no risk of piercing the tissue at the anterior side of the valve.

Figure 3E:
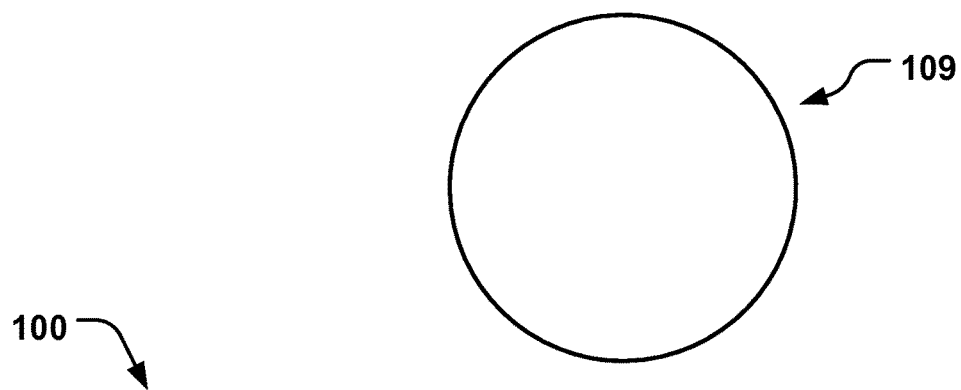
FIGS. 3d-f are schematic illustrations of the cross-sections of the different sections of the annuloplasty implant in FIGS. 3b-c, according to examples of the disclosure.
Figure 3D:
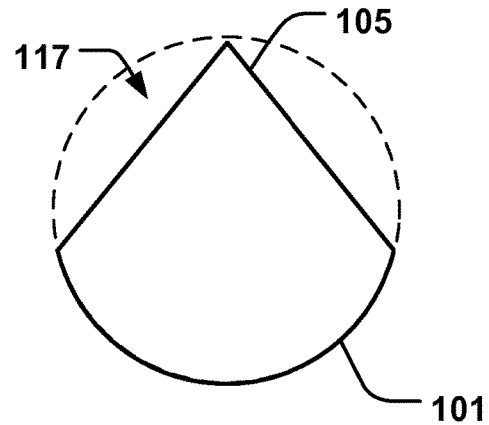
Figure 3F:
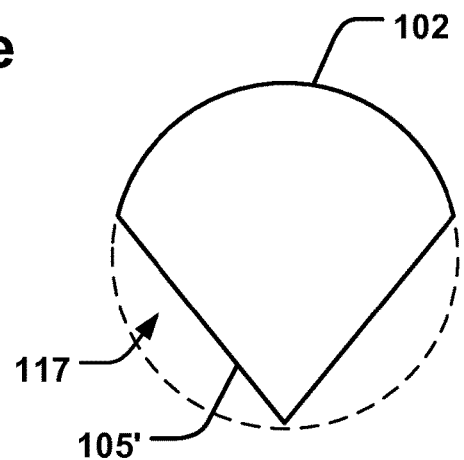

The first retention units 105 may be formed from the material of the first support 101. This may provide for particularly robust and strong first retention units 105. Similarly, the second retention units 105' may be formed from the material of the second support 102. The first and second supports 101, 102, may be integrated and formed from a continuous piece of material. Hence, the first and second retention units 105, 105', may also be formed from such material. The retention units 105, 105', may be cut from the material of the first and second support 101, 102. FIG. 3b shows an example where the retention units 105, 105', are cut from the material of the first and second supports 101, 102. FIG. 3c is a magnified view of FIG. 3b showing an example of different sections of the implant 100. As mentioned, the first support 101 may have the retention units 105 extending in a first direction, and the second support 102 may have the retention units 105' extending in an opposite direction. An intermediate portion 109, without retention units 105, 105', may be positioned therebetween. FIGS. 3e-f show examples of the cross-sections of the implant 100 at the mentioned sections illustrated in FIG. 3c, in the case the retention units 105, 105', are formed from the material of the implant 100. I.e. FIG. 3d shows a cross-section of the first support 101, where material has been removed (indicated by arrow 117 in the figure) from an initially substantially circular support to create tapered retention units 105. FIG. 3e corresponds to the cross-section of the intermediate portion 109, and FIG. 3f shows the cross-section of the second support 102 where material has been cut away to form retention units 105' in the opposite direction. The retention units 105, 105', may be cut to form various shapes for optimizing the gripping force into the tissue. The retention units 105, 105', may be formed by different cutting techniques such as milling or laser cutting techniques. It is also conceivable that the retention units 105, 105', are fixed or integrated onto the respective support 101, 102, by other methods, or by being formed from other materials.

The support 101, 102, may be formed from a solid rod or other solid elongated structure, having various cross-sections, such as circular, elliptic, rhombic, triangular, rectangular etc. The support 101, 102, may be formed from a hollow tube, or other hollow structures with the mentioned cross-sections. The support 101, 102, may be formed from a sandwiched laminate material, comprising several layers of different materials, or different layers of the same material. The support 101, 102, may be formed from a stent or a stent-like structure, and/or a braided material. The support 101, 102, may be formed from a braid of different materials braided together, or from a braid of the same material. As mentioned, the support 101, 102, may be formed from NiTinol, or another suitable bio-compatible material. The surfaces of the first and second supports 101, 102, may be provided with other materials and/or treated with different materials and/or structured to enhance resistance to breaking in case the material is repeatedly bent.

The first and second supports 101, 102, may have respective free ends 111, 111', configured to be arranged on opposite sides of the native heart valve leaflets, in the coiled configuration, as illustrated in e.g. FIGS. 1-2. The two free ends 111, 111', may be displaced from each other with a peripheral off-set distance 112 extending in a coil plane 113, as schematically illustrated in FIG. 4. The coil plane 113 is substantially parallel to an annular periphery 114 of the coil and perpendicular to the axial direction 103. The coil plane 113 accordingly corresponds to the plane spanned by the annular periphery 1114 of the implant 100 when assuming the coiled configuration. The peripheral off-set distance 112 between the two free ends 111, 111', thus extends substantially perpendicular to the central axis 103. This means that, when the implant 100 is positioned in the implanted state, around the annulus of the heart valve, the two free ends will be separated along the plane of the valve. By having such off-set 112 in the plane of the valve, the resulting reduced length of the first or second support member 101, 102, will allow for reducing the number of retention units 105, 105', required to securely fixate the implant 100 at the valve, while at the same time providing for a sufficient overlap of the first and second support member 101, 102, on the opposites sides of the valve to attain a sufficiently strong pinching effect therebetween to fixate the annulus in a modified shape. In situations, placing retention units 105, 105', on the anterior side may be associated with high risk, as discussed above. This can therefore be avoided, by having the off-set 112 as specified. Furthermore, the interference of the implant 100 with the movements of the valve will be minimized. Fastening of the implant 100 on the atrial side can thus be accomplished by fixation of the posterior bow 108, and there will be no interference on the atrial side with the movement of the valve, due to the off-set distance 112 reducing the circle sector of the first support 101.

The off-set distance 112 may correspond to a determined circle sector 115 of the annular periphery 114 by which the two free ends 111, 111', are separated. Hence, the determined circle sector 115 may overlap with the anterior portion 109 in the coiled configuration. The length of the circle sector 115 and the associated distance by which the two free ends 111, 111', are separated may be varied to accommodate various applications and procedures, and be tailored to various anatomies. It is thus possible to provide a highly compliant implant 100 with a minimum of interference with the natural movements of the heart, and which can be secured more easily via retention units 105, 105'.

Figures 10A, 10B:
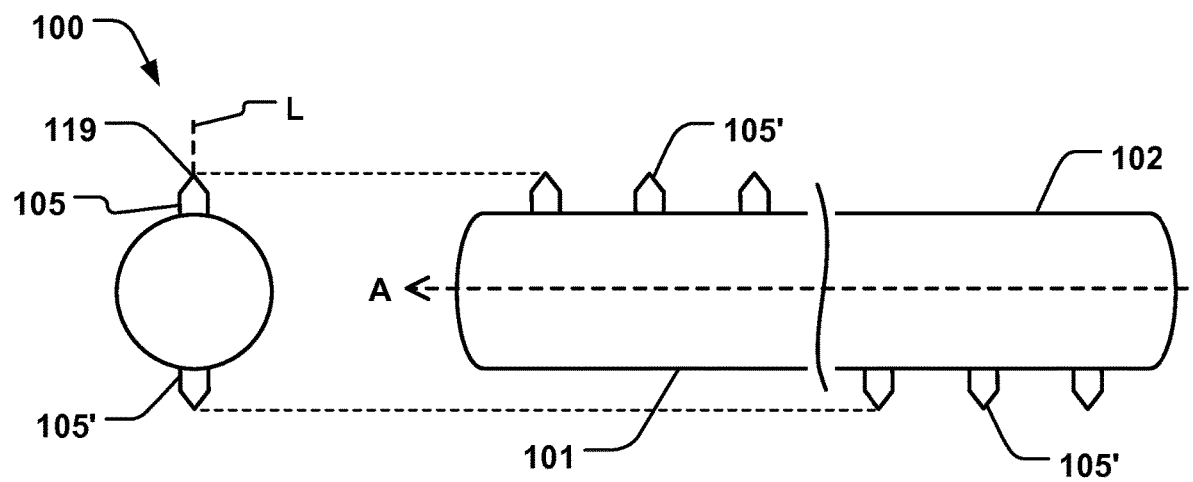
FIGS. 10a-b are schematic illustrations of an annuloplasty implant, in a cross-sectional view (10a), and in a side view (10b), respectively, according to examples of the disclosure.

The first retention units 105 and/or the second retention units 105' may extend in a longitudinal direction (L), and comprise a distal surface 118 forming a tapering shape towards a piercing edge 119, as schematically illustrated in the example of FIG. 8c. This provides for robust retention units 105, 105', allowing for effective grip into the surrounding tissue. The distal surface 118 may extend across the full width (w) of the retention unit 105, 105', so that the piercing edge 119 is positioned at the periphery of the width (w) as shown in the example of FIG. 8c. Alternatively, the retention units 105, 105', may be tapered towards a central piercing edge 119 as shown in the example of FIGS. 10a-b. In this case, the distal surface 118 may comprise two oppositely chamfered surfaces being joined along the centrally located piercing edge 119. Alternatively, the retention units 105, 105', may comprise a conically tapering surface that narrows towards a centrally located piercing edge or tip 119 like a needle. Turning again to FIGS. 8a-c, the distal surface 109 extends in a plane having a normal axis (N) forming an acute angle ($\alpha$) with the longitudinal direction (L). This provides for a robust retention unit 105, 105', while facilitating manufacturing thereof.

The first and second supports 101, 102, extend with an elongated shape along an axial direction (A), as schematically illustrated in e.g. FIG. 8b. The first and second supports 101, 102, are shown in the elongated stretched state, as in FIG. 3a, for a clearer presentation. The normal axis (N) may be substantially parallel with a plane spanned by the axial direction (A) and the longitudinal direction (L), as schematically illustrated in FIGS. 8b-c. This allows for arranging the piercing edge 119 so it extends transverse to the axial direction (A), and also transverse to a surrounding delivery catheter, when arranged therein, which may be advantageous in some applications when the implant 100 is delivered to the annulus. Any risk of wear or damage to the surrounding catheter may be reduced in such case.

The axial direction (A) is perpendicular to a radial direction (R) of the first and second supports 101, 102, as shown in FIGS. 9a-b. In this example, the normal axis (N) is substantially parallel with a plane spanned by the radial direction (R) and the longitudinal direction (L). This may provide for an enhanced grip in the surrounding tissue when the implant 100 is in the coiled shape around the annulus of the heart valve. The direction along which the piercing edge 119 extends may thus be aligned with the axial direction (A), which provides for an improved retention force into the tissue, as the tissue strive to move in a direction perpendicular to the axial direction (A) as the heart is beating, and when the implant 100 is in the coiled shape. The implant 100 may be coiled so that the radial direction (R) is directed from the center of the heart valve towards the annulus. In other situations, the implant 100 may be coiled so that the radial direction (R) is directed from the annulus to the center of the heart valve. As shown in the example of FIG. 9a, the shape of the second retention units 105' may be symmetric with the first retention units 105 with respect to the radial direction (R). It should be understood however that in some applications it may be advantageous to have respective vector components of the normal axis (N) along the radial direction (R) of the first and second retention units 105, 105', oppositely directed with respect to the radial direction (R).

Figures 11A, 11B:
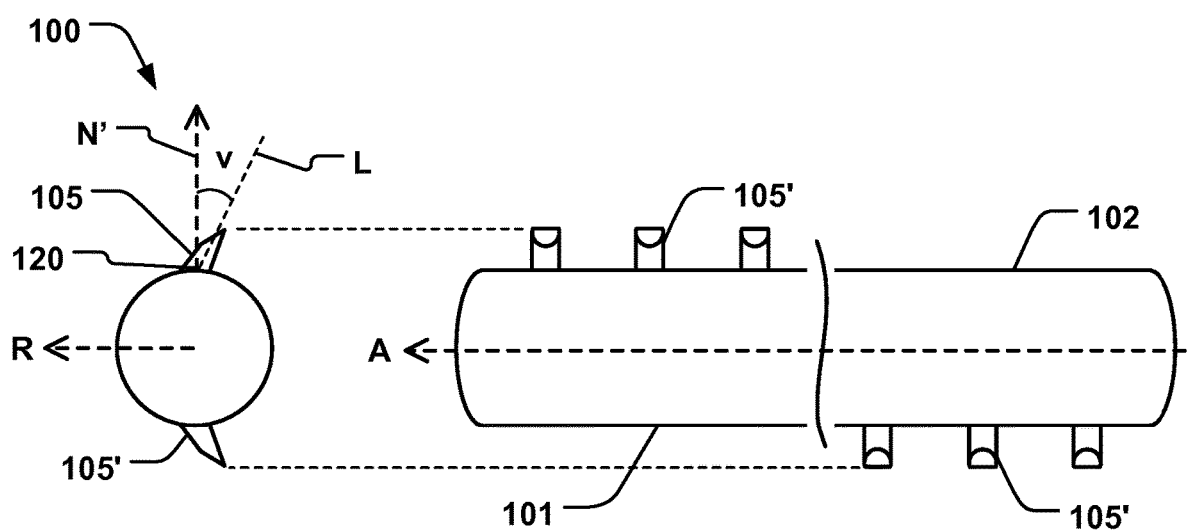
FIGS. 11a-b are schematic illustrations of an annuloplasty implant, in a cross-sectional view (11a), and in a side view (11b), respectively, according to examples of the disclosure.

The longitudinal direction (L) may extend with an angle (v), such as an acute angle (v), relative a normal axis (N') of a surface 120 of the first and/or second supports 101, 102, to which the first retention units 105 and/or the second retention units 105' are fixed, as schematically illustrated in FIG. 11a. Having such angled retention units 105, 105', may provide for a further improved anchoring effect into the tissue and reduce the risk of dislocation between the retention units 105, 105', and the annulus. As in the previously described example, the implant 100 may be coiled so that the radial direction (R) is directed from the center of the heart valve towards the annulus. This may provide for further reducing the risk of having the annulus tissue to move relative the implant 100 in the radial direction (R) as the heart is beating. In other situations, the implant 100 may be coiled so that the radial direction (R) is directed from the annulus to the center of the heart valve. As shown in the example of FIG. 11a, the shape of the second retention units 105' may be symmetric with the first retention units 105 with respect to an axis of symmetry around the radial direction (R). It should be understood however that in some applications it may be advantageous to have respective vector components of the normal axis (N) along the radial direction (R) of the first and second retention units 105, 105', oppositely directed with respect to the radial direction (R).

The first retention units 105 and/or the second retention units 105' may be movable relative a normal axis (N') of surface 120 of the first and/or second supports 101, 102, to which the first retention units 105 and/or the second retention units 105' are fixed. The first retention units 105 and/or the second retention units 105' may be movable by being flexible. This provides for e.g. delivering the implant 100 in a more compact cross-sectional shape through a catheter, having the retention units 105, 105', deflected with a greater angle relative the normal axis (N'). Then, as the implant 100 is ejected from the catheter, the angle may be reduced so that the retention units 105, 105', extend a greater distance from the surface 120, for facilitated piercing into the tissue. The retention units 105, 105', may deflect with an angle (v) towards the radial direction (R) as shown in FIG. 11a, or with an angle (α) towards the axial direction (A) as shown in FIG. 8b-c. The first retention units 105 and/or the second retention units 105' may be movable by being formed by a shape memory material which changes shape over time, e.g. when being heated to an activation temperature.

The height (h) of the retention units 105, 105', may be in the range 0.5-2 mm, which may provide for a particularly advantageous grip into the tissue, while at the same time allowing for a facilitated delivery of the implant 100 from a delivery catheter to the annulus of the heart valve. The first and second retention units 105, 105', may be evenly separated along the length of the respective first and second supports 101, 102. The spacing between adjacent retention units 105, 105', may be in the range 0.5-2 mm. The spacing between adjacent retention units 105, 105', may also be in the range 1-1.5 mm, which may provide for a particularly advantageous anchoring into the tissue.

Figure 6A:
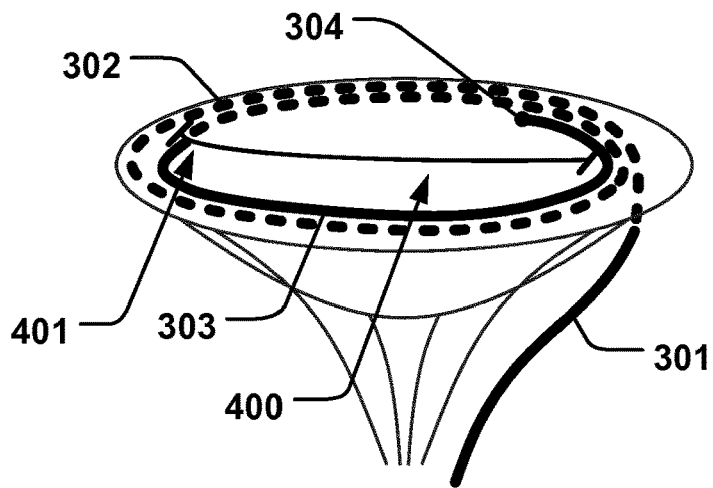
FIG. 6a is a schematic illustration of an arrangement of a delivery device in a method according to one example, where the delivery device has been initially advanced to the ventricle to form a first curve on a ventricular side of the heart valve and a second curve on an atrial side thereof.
Figure 6B:
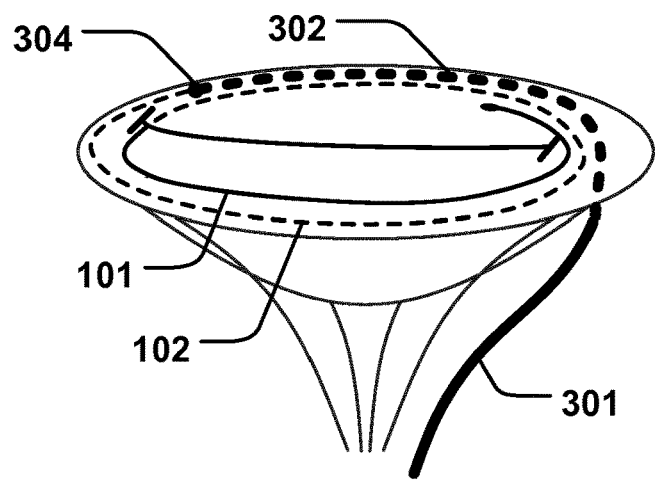
FIG. 6b is a schematic illustration of an arrangement of a delivery device in a method according to one example, where an annuloplasty implant has been ejected on the atrial and ventricular side while retracting the delivery device.
Figure 6C:
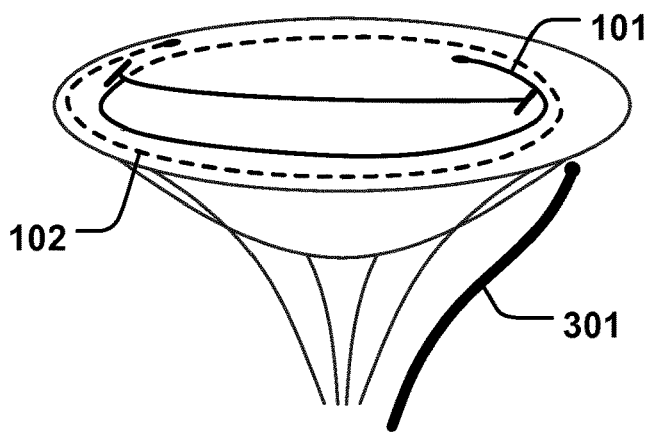
FIG. 6c is a schematic illustration of an arrangement of a delivery device in a method according to one example, where the delivery device has been further retracted and the annuloplasty implant contacts the heart valve on the atrial and ventricular side thereof.
Figure 7A:
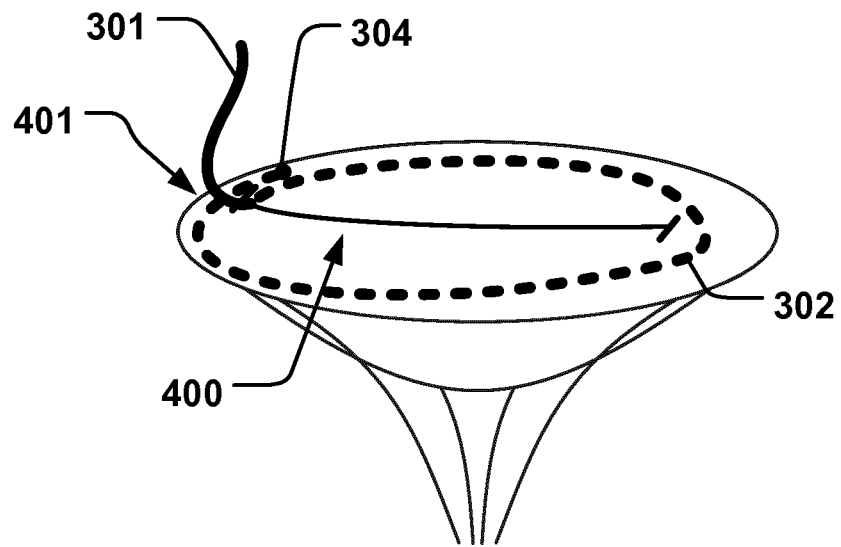
FIG. 7a is a schematic illustration of an arrangement of a delivery device in a method according to one example, where the delivery device has been initially advanced to the atrium to form a first curve on a ventricular side of the heart valve.
Figure 7B:
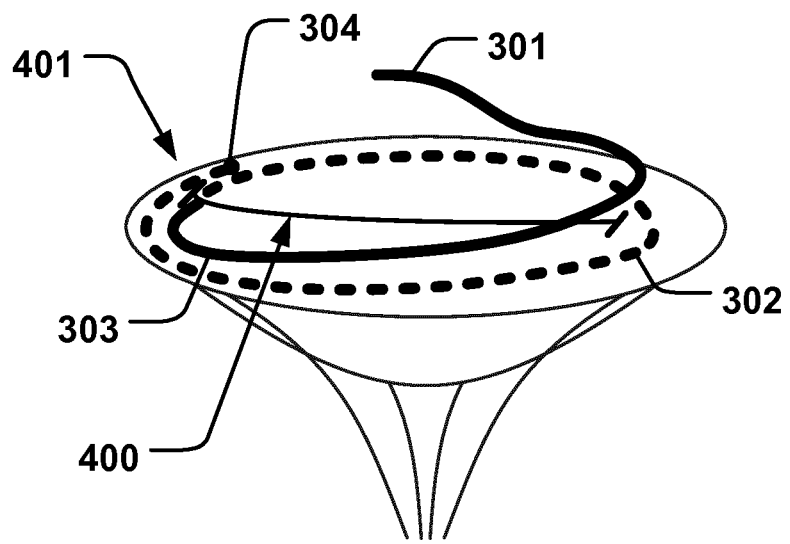
FIG. 7b is a schematic illustration of an arrangement of a delivery device in a method according to one example, where the delivery device forms a second curve on an atrial side of the heart valve.
Figure 7C:
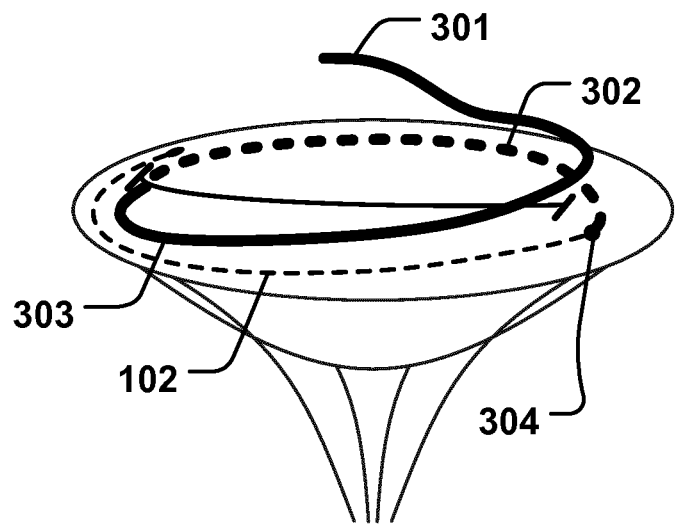
FIG. 7c is a schematic illustration of an arrangement of a delivery device in a method according to one example, where an annuloplasty implant has been ejected on the ventricular side while retracting the delivery device.
Figure 12A:
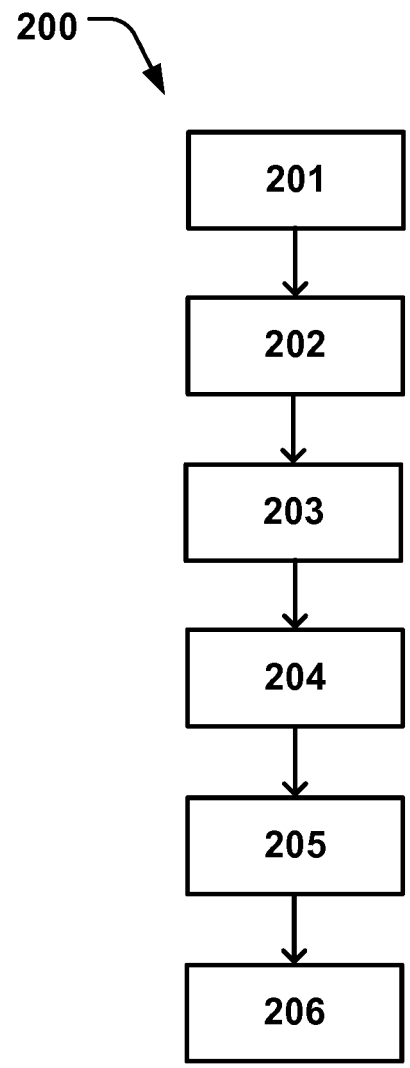
FIG. 12a is a flow chart of a method of repairing a defective heart valve according to one example.

A method 200 of repairing a defective heart valve is disclosed. The method 200 is schematically illustrated in FIG. 12a, in conjunction with FIGS. 6a-c and FIGS. 7a-d. The order in which the steps are described should not be construed as limiting, and it is conceivable that the order of the steps may be varied depending on the particular procedure. The method 200 comprises directing 201 an implant delivery catheter 301 to form 202 a first curve 302 of the implant delivery catheter 301 around the heart valve at a first side of native heart valve leaflets thereof. FIGS. 6a-c illustrate an example where the delivery catheter 301 is first advanced to the ventricular side of the heart, and FIGS. 7a-c illustrate an example where the delivery catheter 301 is initially advanced to the atrial side of the heart. Regardless, the method 200 further comprises forming 203 a second curve 303 of the delivery catheter 301 around the heart valve on a second side of the heart valve leaflets, opposite the first side. The described positioning of the delivery catheter 301 may be preceded by the positioning of a guide wire (not shown) along corresponding first and second curves 302, 303. Thus, the delivery catheter 301 may then be advanced over the guide wire, to assume the first and second curves 302, 303, around the valve on either side of the leaflets thereof. The method 200 comprises ejecting 204 an annuloplasty implant 100 from the delivery catheter 301 while retracting 205 the delivery catheter 301 such that the annuloplasty implant 100 is arranged along the first and second curve 302, 303, on the first and second sides. Retention units 105, 105', arranged on the annuloplasty implant 100 are thereby engaged 206 into tissue of the heart valve from both the first side and the second side when the delivery catheter 301 is retracted. This provides for positioning the retention units 105, 105', in the correct position at both sides of the valve, without having the risk of damaging the tissue, which otherwise could be the case if the implant 100 and retention units 105, 105', thereof would be exposed to the tissue while positioning the implant. Tearing and undesired puncturing of the tissue is thus avoided. A more reliable and secure positioning of the implant 100 at the heart valve 400 is thus achieved.

The annuloplasty implant 100 may be arranged in the delivery catheter 301 along the distal portion of the delivery catheter 301 being bent along the first and second curves 302, 303. Hence, the annuloplasty implant 100 may be bent along the first and second curves 302, 303, simultaneously with the delivery catheter 301. Alternatively, the annuloplasty implant 100 may be advanced into the mentioned distal portion of the delivery catheter 301 after the latter has been formed to assume the first and second curves 302, 303, and after retraction of the guide wire from the delivery catheter 301, if a guide wire has been used as described above. Regardless, the annuloplasty implant 100 is further ejected out from the distal portion while retracting the delivery catheter 301 as explained above and further below with reference to FIGS. 6a-c, 7a-c. I.e. the implant 100 remains substantially stationary in the coiled position (defined by the first and second curves 302, 303) with respect to the valve when the delivery catheter 301 is retracted. The delivery catheter 301 thus defines a path for the implant 100 that allows for facilitated positioning thereof without having to navigate the implant 100 into the correct position at the valve. This also provides for an atraumatic positioning of the implant 100.

As mentioned, with reference to FIGS. 6a-c, the first side may be a ventricular side of the heart, and the second side may be the atrial side of the heart. The portions of the delivery catheter 301 arranged on the ventricular side are indicated with dashed lines in FIGS. 6a-b. The first curve 302 of the implant delivery catheter 301 is arranged around chordae of the heart valve on the ventricular side, and the second curve 303 of the delivery catheter 301 is arranged along an annulus of the heart valve on the atrial side. The heart valve may be the mitral valve, and the ventricle may thus be the left ventricle. The method 200 may comprise positioning the delivery catheter 301 in the ventricle by accessing the ventricle through the apex of the heart with an introducer (not shown). The delivery catheter 301 may then then be inserted through the introducer. Alternatively, the method 200 may comprise positioning the delivery catheter 301 in the ventricle by accessing the ventricle through the aortic valve, or by creating access to the left ventricle through the ventricular septum between the right and left ventricle. Regardless, the method 200 comprises in this example forming a first curve 302 of the implant delivery catheter 301 around the chordae of the heart valve on a ventricular side of the heart valve 400. The delivery catheter 301 may thus be first navigated to the ventricular space between the chordae and the heart muscle, so that the delivery catheter 301 can be curved around the chordae on the ventricular side. The method 200 may comprise inserting the implant delivery catheter 301 through the heart valve 400 to an atrial side thereof, and forming 203 a second curve 303 of the delivery catheter along an annulus of the heart valve on the atrial side. The delivery catheter 301 may be advanced such that annulus is followed in a counter-clockwise direction. In the example of FIG. 6a, the delivery catheter 301 has been inserted through the heart valve 400 to form the second curve 303 on the atrial side. Parts of the delivery catheter 301 on the atrial side has been illustrated with a solid line for clarity of presentation. In FIG. 6a, the delivery catheter 301 has been advanced through the valve 400 at the commissure 401, and with a distal tip 304 of the delivery catheter 301 positioned as illustrated in FIG. 6a, adjacent the opposite commissure.

The method 200 comprises ejecting 204 the annuloplasty implant 100 from the delivery catheter 301 while retracting 205 the delivery catheter 301 such that the annuloplasty implant 100 is arranged along the first and second curve on the ventricular and atrial side. FIG. 6b illustrates an example where the implant 100 has been ejected and the delivery catheter 301 has been retracted back from the atrial side, and through the valve, now having the distal tip 304 arranged at the ventricular side, ready to release the implant 100. Portions of the implant 100 on the atrial side are illustrated with solid lines, and portions of the implant 100 on the ventricular side are illustrated with dashed lines. The implant 100 is thus abutting the valve tissue on the ventricular and atrial sides of the valve 400. The retention units 105, 105', arranged on the annuloplasty implant 100 are thus engaged 206 into tissue of the heart valve from both the ventricular side and the atrial side when the delivery catheter 301 is retracted. FIG. 6*c* shows the retracted delivery catheter 301 having released the implant 100. The retention units 105, 105', are not shown in FIGS. 6*a-c* for clarity of presentation, but the positions of the retention units 105, 105', in FIG. 6*c* corresponds to the illustration in FIG. 2 in this regard. Since the delivery catheter 301 is simultaneously retracted along the curvature of the first and second curve 302, 303, when ejecting the implant 100, the positioning of the implant 100 will effectively correspond to withdrawing the delivery catheter 301 as a sheath previously covering the implant 100 which already is arranged along the curvature provided by the delivery catheter 301 when forming the first and second curve 302, 303, thereof. Hence, the delivery catheter 301 can effectively serve as a guide for the implant 100 for the positioning thereof on the ventricular and atrial side, without having to navigate the implant 100 into the correct position after being ejected from the delivery catheter 301. This provides for improving the control of the positioning of the implant 100, since otherwise, as soon as an implant is ejected from a delivery catheter, the amount of control and steerability on the ejected part is diminished by the decoupling from the physical constrain of the catheter. Positioning the implant 100 as described above removes the steerability requirement on the implant 100 after being ejected, due to the guiding of the implant 100 to the final position, while being fully confined within the delivery catheter 301. This also minimizes the risk of interference with the surrounding anatomy, such as entanglement of the implant with the chordae. This also provides for positioning the retention units 105, 105', in the correct position at the valve, without having the risk of damaging the tissue, which otherwise could be the case if the implant 100 and retention units 105, 105', thereof would be exposed to the tissue while positioning the implant. Tearing and undesired puncturing of the tissue is thus avoided. A more reliable and secure positioning of the implant 100 at the heart valve 400 is thus achieved.

Figure 7D:
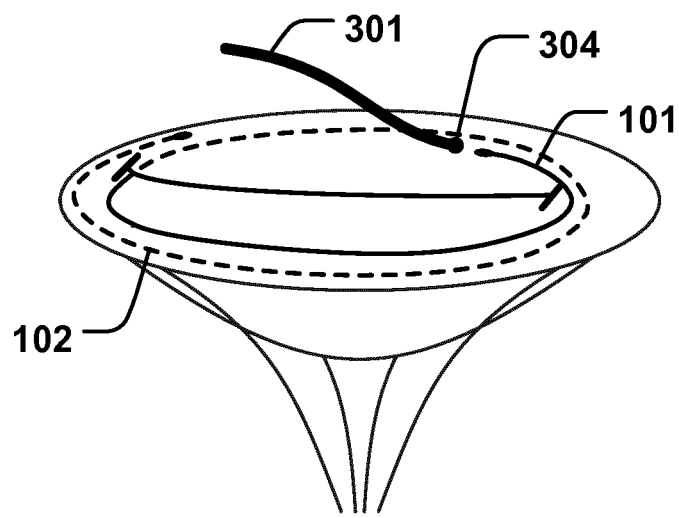
FIG. 7d is a schematic illustration of an arrangement of a delivery device in a method according to one example, where the delivery device has been further retracted and the annuloplasty implant contacts the heart valve on the atrial and ventricular side thereof.

As shown in the example of FIGS. 7*a-c*, the delivery catheter 301 may be initially positioned in the atrium, via access through the atrial septum, and directed to the anterior commissure 401. A first curve 302 of the delivery catheter 301 is arranged around chordae of the heart valve on the ventricular side, again returning to the anterior commissure 401 (FIG. 7*a*). A second curve 303 of the implant delivery catheter 301 is arranged along an annulus of the heart valve on the atrial side. Again, portions of the implant 100 on the atrial side are illustrated with solid lines, and portions of the implant 100 on the ventricular side are illustrated with dashed lines. As mentioned above, a guide wire (not shown) may be arranged in the shape of the first and second curves 302, 303, before advancing the delivery catheter 301 over the guide wire to assume the corresponding shapes on both sides of the valve leaflets. The guide wire and the delivery catheter be initially advanced into the atrium via access through the atrial septum of the heart. FIG. 7*a* shows the delivery catheter 301 forming the first curve 302 around the valve on the ventricular side, and the distal tip 304 is positioned on the ventricular side. FIG. 7*b* shows the second curve 303 formed at least partly around the annulus on the atrial side. FIG. 7*c* shows the delivery catheter 301 partly retracted (see e.g. new position of distal tip 304 on ventricular side), exposing part of a support ring 102 of the annuloplasty implant 100 on the ventricular side. The retention units 105 on the second support ring 102 (not shown for clarity of presentation) are thus exposed and can be advanced into the tissue as the delivery catheter 301 is gradually retracted. FIG. 7*d* shows the annuloplasty implant 100 just being fully released from the distal tip 304 of the delivery catheter 301, so that first and second supports 101, 102, of the annuloplasty implant 100 are arranged to contact opposite sides of the valve. The retention units 105, 105', (not included in the illustrations of FIGS. 7*a-c* for clarity of presentation) arranged on the annuloplasty implant 100 are thus engaged 207 into tissue of the heart valve from both the ventricular side and the atrial side when the delivery catheter 301 is retracted, without risk of damaging the tissue, since there is no rotational movement of the implant 100 with respect to the tissue. Further, as with the example in FIGS. 6*a-c*, the delivery catheter 301 can effectively serve as a guide for the implant 100 for the positioning thereof on the ventricular and atrial side, without having to navigate the implant 100 into the correct position after being ejected from the delivery catheter 301. This provides for improving the control of the positioning of the implant 100. Similarly as described above, a guide wire may be first advanced to assume the first and second curves 302, 303, and the delivery catheter 301 may then be advanced over the guide wire to assume a coiled configuration. The guide wire may then be removed, and the implant 100 may be inserted into the delivery catheter 301, and thereby guided to assume the coiled configuration of the delivery catheter, which then can be retracted to expose the implant 100 which can retain the coiled configuration due to a shape memory of the material thereof.

Figure 12B:
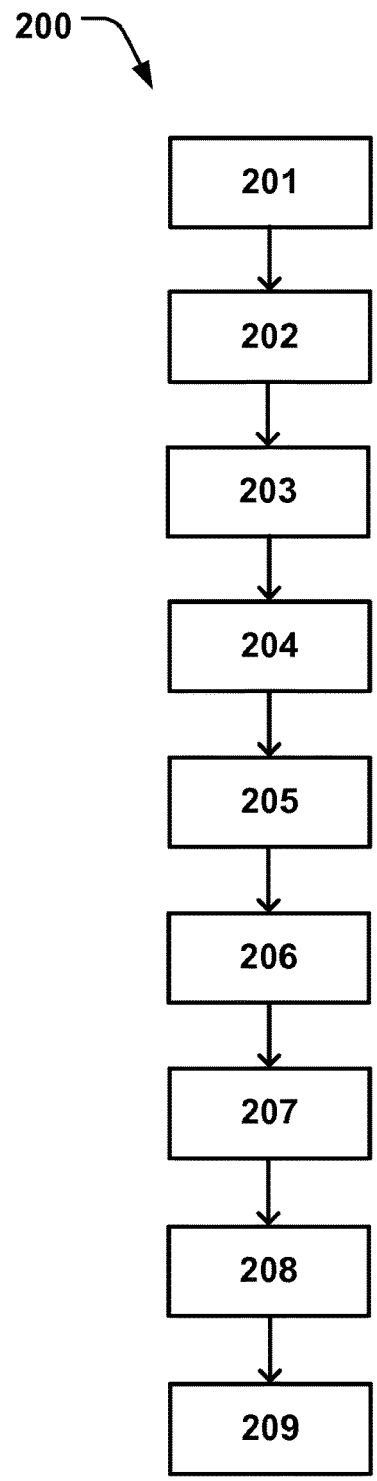
FIG. 12b is another flow chart of a method of repairing a defective heart valve according to one example.

FIG. 12*b* illustrates a further flow chart of a method 200 of repairing a defective heart valve. The order in which the steps of the method 200 are illustrated should not be construed as limiting and it is conceivable that the order in which the steps of the method 200 is carried out may be varied.

In the method 200, the annuloplasty implant 100 may be kept substantially stationary in relation to the heart valve 400 when being ejected from the delivery catheter 301 while simultaneously retracting the delivery catheter 301 in relation to the annuloplasty implant 100. As elucidated above, this facilitates positioning of the retention units 105, 105', without risking damaging the tissue.

The annuloplasty implant 100 may have a predefined shape having a curvature corresponding substantially to the first and second curve 302, 303, such that, when ejected from the delivery catheter 301, the annuloplasty implant 100 is arranged 207 along the first and second curve 302, 303, as a coil or helix in a coiled configuration, as illustrated in FIGS. 6*a-c*, 7*a-d*. The first and second curve 302, 303, may thus form two continuously connected loops, on opposite sides of the heart valve, being connected through the commissure 401. This provides for achieving an efficient deployment of an annuloplasty implant 100 around the annulus of the valve 400, on both the ventricular and atrial sides.

By having a predefined ring-shape approximating the curvature of the first and second curves 302, 303, of the delivery catheter 301, the annuloplasty implant 100 may be readily aligned around the heart valve 400 along the extension of the first and second curves 302, 303, when the implant 100 is ejected and the delivery catheter is simultaneously withdrawn, with a minimum of movement of the implant 100 relative to the valve 400 when the delivery catheter 301 is withdrawn. A more stable and controlled positioning of the implant 400 along the annulus of the heart valve 400 may thus be achieved. The predefined ring-shape of the implant 100 can be determined for example by a heat treatment procedure during manufacturing of the implant 100. When the implant is confined in the delivery catheter 301, it assumes an elongated configuration, until it is ejected, whereby it assumes the predefined shape, i.e. the relaxed shape of the shape-memory of the material from which the ring is formed. As mentioned above, the implant 100 may subsequently also assumed a contracted shape where the distance between supports 101, 102, is further reduced in the axial direction 103, e.g. by the increase of temperature to an activation temperature. This further facilitates fixation of the retention units 105, 105', into the tissue. It is conceivable that the delivery catheter 301 is withdrawn gradually to slowly expose the retention units 105, 105', and allow the temperature of the supports 101, 102, to increase, so that the retention units 105, 105' can be gradually pushed into the tissue as the catheter 301 is withdrawn. This provides for increasing the control by which the implant is attached at the valve, hence allowing for a safer implantation procedure.

Hence, the method 200, in both examples of FIGS. 6a-c and FIGS. 7a-d, a first support ring 101 of the coil may be positioned on the atrial side and a second support ring 102 of the coil is positioned on the opposite ventricular side when ejecting the annuloplasty implant from the delivery catheter while retracting the delivery catheter, whereby leaflets of the heart valve are pinched between the first and second support rings 101, 102, and the retention units 105, 105', are anchored 208 into the tissue.

And the method 200 may comprise activating 209 a contracted state of the annuloplasty implant 100 so that a first pitch distance ($p_1$) between the first and second support rings 101, 102, is reduced to a second pitch distance ($p_2$), whereby the first and second support rings 101, 102, move towards each other so that the retention units 105, 105', are pushed into the tissue.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty implant comprising
first and second supports being adapted to be arranged as a coil in a coiled configuration around an axial direction, wherein the first and second supports are adapted to be arranged on opposite sides of native heart valve leaflets of a heart valve,
wherein the first support comprises first retention units integrated with the first support at a pre-defined position whereby the first retention units are fixed to an outer surface of the first support and arranged along at least a first retention portion thereof,
wherein the second support comprises second retention units integrated with the second support at a pre-defined position whereby the second retention units are fixed to an outer surface of the second support and arranged along at least a second retention portion thereof,
wherein the first and second retention portions are curved in the coiled configuration,
wherein the first and second retention units extend from respective first and second retention portions to produce a retention force, in use, at both of said opposite sides,
wherein the first support is adapted to be arranged on an atrial side of said heart valve, and the second support is adapted to be arranged on a ventricular side of the heart valve,
wherein the first support comprises a first posterior bow and the second support comprises a second posterior bow, wherein the first and second posterior bows are adapted to conform to a posterior aspect of said heart valve,
wherein the first and second retention units are arranged on respective first and second posterior bows, and
wherein the first and second posterior bows are separated by an intermediate anterior portion, wherein the first and second retention units are arranged with an off-set distance from the anterior portion towards respective first and second posterior bows, whereby the anterior portion comprises a smooth surface free from retention units.

2. The annuloplasty implant according to claim 1, wherein the first retention units extend from the first retention portion in a direction towards the second support.

3. The annuloplasty implant according to claim 1, wherein the second retention units extend from the second retention portion in a direction towards the first support.

4. The annuloplasty implant according to claim 2, wherein the first and second retention units extend in opposite directions along the axial direction.

5. The annuloplasty implant according to claim 1, wherein the first and second supports are separated with a first pitch distance ($p_1$) in the axial direction, in the coiled configuration, and wherein the first and/or second support comprises a shape-memory material configured to assume a contracted state having a second pitch distance ($p_2$) in the axial direction being shorter than the first pitch distance.

6. The annuloplasty implant according to claim 5, wherein the shape-memory material is configured to assume said contracted state in response to an activation temperature.

7. The annuloplasty implant according to claim 5, wherein the first and second supports are configured to engage with a restraining unit at a separation at the first pitch distance and to assume the contracted state upon removal of the restraining unit.

8. The annuloplasty implant according to claim 1, wherein at least part of the first retention units are displaced in a direction along an annular periphery of the coil in relation to at least part of the second retention units, whereby a line extending from a first retention unit, parallel with the axial direction, intersects the annular periphery of the second support at a position between two second retention units.

9. The annuloplasty implant according to claim 1, wherein at least part of the first and second retention units comprise a shape that tapers in a direction from the respective first and second retention portions.

10. The annuloplasty implant according to claim 1, wherein the first retention units are formed from the material of the first support, and/or the second retention units are formed from the material of the second support.

11. The annuloplasty implant according to claim 1, wherein the support is formed from a solid rod, and/or a sandwiched laminate material, and/or a hollow tube, and/or a stent, and/or a braided material.

12. The annuloplasty implant according to claim 1, wherein the first and second supports have respective free ends configured to be arranged on opposite sides of the native heart valve leaflets, in the coiled configuration, whereby the two free ends are displaced from each other with a peripheral off-set distance extending in a coil plane, said coil plane being substantially parallel to an annular periphery of said coil and perpendicular to said axial direction.

13. The annuloplasty implant according to claim 12, wherein the off-set distance corresponds to a determined circle sector of said annular periphery by which said two free ends are separated, and wherein the determined circle sector overlaps with the anterior portion in the coiled configuration.

14. The annuloplasty implant according to claim 1, wherein the first retention units and/or the second retention units are elongated in a longitudinal direction (L) extending from the respective first and second retention portions, the first retention units and/or the second retention units comprising a distal surface forming a tapering shape towards a piercing edge, wherein the distal surface extends in a plane having a normal axis (N) forming an acute angle (a) with the longitudinal direction.

15. The annuloplasty implant according to claim 14, wherein the first and second supports extend with an elongated shape along a second axial direction (A), wherein the normal axis (N) is substantially parallel with a plane spanned by the axial direction (A) and the longitudinal direction (L).

16. The annuloplasty implant according to claim 14, wherein the first and second supports extend with an elongated shape along a second axial direction (A), being perpendicular to a radial direction (R) thereof, wherein the normal axis (N) is substantially parallel with a plane spanned by the radial direction (R) and the longitudinal direction (L).

17. The annuloplasty implant according to claim 14, wherein the first and second supports extend with an elongated shape along a second axial direction (A), and wherein the longitudinal direction (L) extends with an angle (v) relative a normal axis (N') of surface of the first and/or second supports to which the first retention units and/or the second retention units are fixed.

18. The annuloplasty implant according to claim 1, wherein the first retention units and/or the second retention units are movable relative a normal axis (N') of surface of the first and/or second supports to which the first retention units and/or the second retention units are fixed.

19. A method of repairing a defective heart valve comprising;
    directing an implant delivery catheter to form a first curve of the implant delivery catheter around the heart valve at a first side of native heart valve leaflets thereof,
    forming a second curve of the delivery catheter around the heart valve on a second side of the heart valve leaflets opposite the first side, and
    ejecting an annuloplasty implant from the delivery catheter while retracting the delivery catheter such that the annuloplasty implant is arranged along the first and second curve on the first and second sides,
    whereby retention units arranged on the annuloplasty implant are engaged into tissue of the heart valve from both the first side and the second side when the delivery catheter is retracted,
    wherein the annuloplasty implant has a predefined shape having a curvature corresponding substantially to the first and second curve, such that, when ejected from the delivery catheter, the annuloplasty implant is arranged along the first and second curve as a coil in a coiled configuration,
    wherein a first support ring of the coil is positioned on an atrial side and a second support ring of the coil is positioned on an opposite ventricular side when ejecting the annuloplasty implant from the delivery catheter while retracting the delivery catheter, whereby leaflets of the heart valve are pinched between the first and second support rings and the retention units are anchored into the tissue,
    wherein the first support ring comprises a first posterior bow and the second support ring comprises a second posterior bow, the first and second posterior bows conform to a posterior aspect of said heart valve,
    wherein the first and second retention units are arranged on respective first and second posterior bows, and
    wherein the first and second posterior bows are separated by an intermediate anterior portion, wherein the first and second retention units are arranged with an off-set distance from the anterior portion towards respective first and second posterior bows, whereby the anterior portion comprises a smooth surface free from retention units.

20. The method according to claim 19, wherein the first side is an atrial side of the heart, and the second side is a ventricular side of the heart, wherein the first curve of the delivery catheter is arranged along an annulus of the heart valve on the atrial side, and wherein the second curve of the implant delivery catheter is arranged around chordae of the heart valve on the ventricular side.

21. The method according to claim 19, wherein the first side is a ventricular side of the heart, and the second side is an atrial side of the heart, wherein the first curve of the implant delivery catheter is arranged around chordae of the heart valve on the ventricular side, and wherein the second curve of the delivery catheter is arranged along an annulus of the heart valve on the atrial side.

22. The method according to claim 19, wherein the annuloplasty implant is kept substantially stationary in relation to the heart valve when being ejected from the delivery catheter while simultaneously retracting the delivery catheter in relation to the annuloplasty implant.

23. The method according to claim 19, comprising activating a contracted state of the annuloplasty implant so that a first pitch distance ($p_1$) between the first and second support rings is reduced to a second pitch distance ($p_2$), whereby the first and second support rings move towards each other so that the retention units are pushed into the tissue.

24. The method according to claim 14, wherein the longitudinal direction (L) extends with an acute angle (v) relative a normal axis (N') of an outer surface of the first and/or second supports.

25. The method according to claim 14, wherein the longitudinal direction (L) extends with right angle relative a normal axis (N') of an outer surface of the first and/or second supports.

* * * * *